United States Patent
Friedman et al.

(10) Patent No.: US 8,409,600 B2
(45) Date of Patent: Apr. 2, 2013

(54) METHODS FOR PREVENTION AND/OR TREATMENT OF CAPSULAR CONTRACTURE

(75) Inventors: Jeanne V. Friedman, Rye, NY (US); Elsa M. Raskin, Greenwich, CT (US)

(73) Assignee: J&E Solutions, LLC, New York, NY (US)

( * ) Notice: Subject to any disclaimer, the term of this patent is extended or adjusted under 35 U.S.C. 154(b) by 662 days.

(21) Appl. No.: 12/617,502

(22) Filed: Nov. 12, 2009

(65) Prior Publication Data

US 2010/0189761 A1 Jul. 29, 2010

Related U.S. Application Data

(60) Provisional application No. 61/146,778, filed on Jan. 23, 2009, provisional application No. 61/183,150, filed on Jun. 2, 2009.

(51) Int. Cl.
*A01N 37/36* (2006.01)
*A61K 31/17* (2006.01)

(52) U.S. Cl. .......... 424/423; 514/159; 514/588
(58) Field of Classification Search .......... 514/159, 514/588

See application file for complete search history.

(56) References Cited

U.S. PATENT DOCUMENTS

| | | |
|---|---|---|
| 6,022,317 A | 2/2000 | Cruanas et al. |
| 7,097,847 B2 | 8/2006 | Reynolds |
| 2003/0027864 A1 | 2/2003 | Guiramand et al. |
| 2007/0196454 A1 | 8/2007 | Stockman et al. |
| 2008/0153900 A1 | 6/2008 | Hunter |

*Primary Examiner* — Jeffrey S. Lundgren
*Assistant Examiner* — Chris Simmons
(74) *Attorney, Agent, or Firm* — Davidson, Davidson & Kappel, LLC

(57) ABSTRACT

Methods for prevention or treatment of capsular contracture following surgical implants and other fibrosis related conditions comprising applying a topical composition comprising a pharmaceutically acceptable keratolytic, a pharmaceutically acceptable protein denaturant, a hydrating agent, and combinations thereof are disclosed.

19 Claims, No Drawings

METHODS FOR PREVENTION AND/OR TREATMENT OF CAPSULAR CONTRACTURE

FIELD OF THE INVENTION

The present application relates to methods for the prevention and/or treatment of capsular contracture in the vicinity of surgical implants, the treatment of irradiated skin, and other fibrosis related conditions.

BACKGROUND

Breast implant capsular contracture remains a significant complication of cosmetic and reconstructive breast surgery. The economic impact of capsular contracture is significant. Rates for both saline and silicone gel implants are 10% for primary cosmetic augmentations and 15 to 30% for reconstruction. There were 347,524 breast augmentations and 43,091 breast reconstructions in the United States in 2007. Therefore, this year alone approximately 47,679 new cases of capsular contracture will be diagnosed. Capsular contracture may also form in the advent of buttocks augmentation surgery and calf augmentation.

Following surgery, capsules form as a normal response around a foreign body (eg. breast implants, pacemakers, orthopedic joint prosthetics). Histologically, the human breast capsular tissue is comprised of an inner layer of fibrocytes and histiocytes, which are surrounded by a thicker layer of collagen bundles arranged in a parallel array. Capsular contracture is an abnormal response of the human immune system to foreign material. In capsular contracture, there is an overgrowth of scar tissue resulting in tightening of the implant. Capsular contracture may become painful and cause distortion of and hardness over the implant The potential etiologies include the hypertrophic scar hypothesis, myofibroblasts, silicone gel bleed, hematoma and infectious theory. Most experts feel that capsular contracture is a multifactoral problem. The best preventative measure is a sound surgical technique. The techniques described below lower the rate of capsular contracture, but do not completely eliminate its formation.

Present preventative measures against capsular contracture are refined surgical techniques including breast pocket irrigations before placement of the implants. Such procedures may include a betadine alternative including a combination of 50 ml of stock betadine solution, 1 g of cefazolin, 80 mg gentamycin and 500 ml normal saline. Although used by many surgeons, betadine irrigation is only recommended by the FDA due to concerns of the silicone shell viability. A nonbetadine alternative involves a triple antibiotic solution combination comprising 50,000 units of bacitracin, 1 g cefazolin, 80 mg gentamicin and 500 ml normal saline.

Other surgical techniques to prevent capsular contracture include atraumatic pocket dissection under direct vision, avoiding blunt instrumentation, irrigation of the pocket with 120 to 150 ml of irrigation without active evacuation, cleansing of skin surrounding incisions with irrigation solution, surgical glove change before implant handling, aseptic implant insertion and minimized implant manipulation after insertion.

Perioperatively, systemic antibiotics, textured implants, glove change before implant handling, aseptic implant insertion and use of post operative drains have been recommended in the prevention of capsular contracture.

Post-operative treatment of capsular contracture includes: Non-surgical treatment (conservative) of capsular contracture such as: administration of high doses of ibuprofen (Advil®), naproxen sodium (Aleve®) or other nonsteroidal antiinflammatory medications; massage, Vitamin E, Off label use of Montelukast sodium (Singulair®) or Zafirlukast (Accolate®), or any combinations of the above. All the above conservative measures have been limited in the number of patients improved with their usage as well as in the scope of the improvement.

Examples of surgical treatment of capsular contracture are surgical dissection of the capsule comprising total capsulectomy (removal) or capsulotomy (release) and change in implant anatomical location (i.e., from subglandular to subpectoral). Recurrence rates following surgical treatment are as high as 50%.

United States Patent Publication No. 20070196454 by Stockman, et al., describes a method where applying cross linked gels comprising polyalkyleneimines to the area between the implant and body tissue to be used as a coating for the breast implant in order to retard or reduce the extent of fibrosis. However, this process involves internal application which may lead to further complications and thus is not a long-lasting solution.

In view of the above difficulties with available procedures, there still exists a need for a simple, noninvasive method for the prevention and treatment of capsular contracture and other fibrosis related conditions.

OBJECTS AND SUMMARY OF PRESENT INVENTION

It is an object of the invention to provide a noninvasive therapy for the prevention and/or treatment of capsular contracture, irradiated skin and other fibrosis related conditions.

It is a further object of the invention to provide a therapy for capsular contracture and irradiated skin which is simple and easy to use, has a low risk of side effects, is convenient, and is affordable.

It is an object of the present invention to treat capsular contracture in a human patient who has developed or is at risk of developing capsular contracture with application of a topical composition.

It is a further object of the present invention to treat capsular contracture in a human patient who has had breast implant surgery with a topical composition so as to reduce the Baker Grade of breast capsular contracture by at least one grade, and at least two grades in certain situations.

In accordance with the above objects and others, the present invention is directed in part to a method of treating capsular contracture and irradiated skin, comprising topically applying to a human on an affected area which has developed or is at risk of developing capsular contracture a topical composition containing an effective amount of a pharmaceutically acceptable and topically active ingredient to treat capsular contracture, the active ingredient selected from the group consisting of a pharmaceutically acceptable keratolytic, a pharmaceutically acceptable protein denaturant, a hydrating agent, and combinations thereof.

In certain preferred embodiments, the invention is directed to a topical formulation which is useful for treating capsular contracture and/or irradiated skin, comprising an active ingredient selected from the group consisting of a pharmaceutically acceptable keratolytic, a pharmaceutically acceptable protein denaturant, a hydrating agent, and combinations thereof; together with a suitable pharmaceutically acceptable excipient(s) for topical application of the active ingredient(s) to the affected area of skin.

In certain preferred embodiments, the topically active agent is selected from the group consisting of urea, salicylic acid, ammonium lactate, and combinations thereof.

In certain preferred embodiments, the topical composition is administered in a form selected from the group consisting of a solution, lotion, gel, foam, cream, ointment and paste. In certain preferred embodiments, the topical composition is a stable, uniform water-washable ointment of a non-aqueous emulsion.

In certain preferred embodiments, the topical composition comprises salicylic acid in a concentration from about 5% to about 30% by weight and urea in a concentration of from about 5% to about 20%. In certain other preferred embodiments, the topical composition comprises ammonium lactate in a concentration from about 5% to about 30% by weight and urea in a concentration of from about 5% to about 20%, and preferably from about 12 to about 15% (w/w).

The invention is directed in part to a method of treating capsular contracture, comprising topically applying to a human on a post-surgical implant area which has developed or is at risk of developing capsular contracture a topical composition comprising from about 5 to about 20% (w/w) urea together with a second active ingredient selected from the group consisting of salicylic acid, ammonium lactate, and combinations thereof.

In further embodiments, the invention is directed to a method of treating capsular contracture, comprising preparing a topical composition comprising from about 5 to about 20% (w/w) urea together with a second active ingredient selected from the group consisting of salicylic acid, ammonium lactate, and combinations thereof as a stable, uniform water-washable ointment of a non-aqueous emulsion, topically applying the topical composition to a human on a post-surgical implant area which has developed or is at risk of developing capsular contracture at least once daily to the affected area which preferably has been cleaned with use of warm/hot water and/or application of mild heat and preferably vigorously massaging the composition into the affected area.

In certain embodiments, the method provides for application of compositions comprising urea and salicylic acid in a water-washable ointment of a non-aqueous emulsion type. Such topical non-aqueous emulsion compositions and the preparation of the same are described in U.S. Pat. No. 7,097,847 ((Reynolds), hereby incorporated by reference in its entirety.

Suitable topical preparations may comprise an emulsion, solution, lotion, gel, foam, cream, ointment or paste.

Present conservative post-operative treatments such anti-inflammatory drugs presently yield a low success rate in the prevention of capsular contracture. Initial reduction in capsular contracture may still be followed by its recurrence as many as ten years postoperatively. Application of the present invention will result in a lower incidence of capsular contracture and in turn prevent surgical intervention of this common complication.

There are currently no over the counter medications proven to prevent or alleviate capsular contracture. The composition of the invention will provide such as an option.

This application is particularly advantageous for its simplicity and ease of use, low risk of side effects, convenience, and affordability.

As quoted in the background statistics, capsular contracture represents a significant health problem with several million women affected worldwide. This invention purposes a low cost solution to a staggering health care problem.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent.

In certain embodiments, the inventive methods described above are further combined with oral anti-inflammatory treatment, for example, effective oral dosages of a non-steroidal anti-inflammatory (NSAID) such as Aspirin, Choline and magnesium salicylates, Choline salicylate, Celecoxib, Diclofenac potassium, Diclofenac sodium, Diclofenac sodium with misoprostol, Diflunisal, Etodolac, Fenoprofen calcium, Flurbiprofen, Ibuprofen, Indomethacin, Ketoprofen, Magnesium salicylate, Meclofenamate sodium, Mefenamic acid, Meloxicam, Nabumetone, Naproxen, Naproxen sodium, Oxaprozin, Piroxicam, Rofecoxib, Salsalate, Sodium salicylate, Sulindac, Tolmetin sodium, and Valdecoxib.

DETAILED DESCRIPTION OF THE INVENTION

The invention is directed to methods of preventing, substantially preventing and treating capsule contracture and other fibrosis related conditions. The inventive methods comprise applying the compositions described herein to the external area surrounding the implant for prevention; the external area surrounding the capsule for treatment. The compositions contemplated for use in the methods of prevention and treatment of the present invention comprise one or more components that aid in hydration (e.g., urea) and/or one or more active agents that have keratolytic activity (e.g., salicylic acid), in a suitable pharmaceutically acceptable topical carrier.

In certain embodiments, the invention involves using a formulation preferably comprised of about 5% salicylic acid and about 10% urea, which formulation was previously used as a skin softener, for the prevention and/or treatment of capsular contracture that may result from the introduction of saline, silicone or other implants into a human patient. These other implants may include, but are not limited to, pacemakers and defibrillators. However, it is believed that compositions having from about 5% to about 30% salicylic acid and from about 5% to about 20% urea will be effective for use in the methods of the present invention. Nevertheless, it has been found that when the percentage amount of urea is from about 12% to to about 20%, the strength of the composition may be increased. Compositions having this enhanced formulation would be used in patients who have a denser capsule or more fatty tissue surrounding such.

In certain embodiments, the compositions used in the inventive methods disclosed herein are described in U.S. Pat. No. 7,097,847, hereby incorporated by reference in its entirety, results in a composition having the percentages of salicylic acid and urea that are set forth above.

Other applications of the invention are for the treatment of irradiated skin, prevention and/or treatment of scar tissue, for the prevention and/or treatment of subcutaneous tissue induration, keloid scar tissue and stretch marks, and to improve the color, texture and general appearance of irradiated skin.

The methods of the present invention for prevention of capsular contracture comprise topical application of the composition using the following steps:

Wash and dry the affected area (that is, the skin surrounding the implant or the skin over the capsular contracture) prior to use.

Apply the composition daily (use sparingly) with vigorous massage to affected area. If necessary, exert compression or pressure when massaging to break up existing capsule. Enhanced absorption is obtained with application of the composition following a hot shower. Occlusive dressing (hydrogel), or tight clothing (sports bras), will also enhance the result. Continued daily use will yield optimal results.

The twice daily application should continue a minimum of 2 to 4 weeks or until there is a return to a grade one capsule or no further continued improvement in capsule softening occurs for a week. Optimal results are best maintained with daily continued application.

Response to this treatment method may vary depending on the stage, composition and timing of capsular contracture as well as the length of twice daily application. Lack of patient compliance will adversely affect the ultimate result. The composition should not be used on infected, irritated or broken skin, or directly on or over a tattoo. Diabetics should use only under a doctor's supervision.

One particularly useful embodiment of the invention involves the use of the topical compositions for the treatment/prevention of capsular contracture in breast surgery (e.g., breast implants). There are four grades of breast capsular contracture—Baker grades I through IV. The Baker grading is as follows:

Grade I—the breast is normally soft and looks natural
Grade II—the breast is a little firm but looks normal
Grade III—the breast is firm and looks abnormal
Grade IV—the breast is hard, painful, and looks abnormal. of developed or is at risk of developing capsular contracture a topical composition.

The inventive treatment of capsular contracture in a human patient who has had breast implant surgery with a topical composition as disclosed herein preferably reduces the Baker Grade of breast capsular contracture by at least one grade, and preferably at least two grades, when the application instructions set forth herein are followed.

In a broader sense, the invention is directed in part to a method of treating capsular contracture, comprising applying topically applying to a human on an affected area which has developed or is at risk of developing capsular contracture a topical composition containing an effective amount of a pharmaceutically acceptable and topically active ingredient to treat capsular contracture, the active ingredient selected from the group consisting of a pharmaceutically acceptable keratolytic, a pharmaceutically acceptable protein denaturant, and combinations thereof.

For the purposes of this invention it is to be understood that characterizing a component within a particular category does not mean the agent does not have other functions within the compositions of the invention. For example, designating urea as a protein denaturant does not mean that it cannot also perform another function, e.g., urea is also believed to have keratolytic activity. Thus, for purposes of the present invention, it should be understood that one ingredient can have multiple functions, including both keratolytic and protein denaturant activity.

Agents that have keratolytic activity contemplated for use in the invention may include, but are not limited to urea, alpha-hydroxy acids, selected from the group consisting of agaricic acid, aleuritic acid, allaric acid, aitraric acid, arabiraric acid, ascorbic acid, atrolactic acid, benzilic acid, citramalic acid, citric acid, dihydroxytartaric acid, erythraric acid, galactaric acid, galacturonic acid, glucaric acid, glucuronic acid, glyceric acid, glycolic acid, gularic acid, gulonic acid, hydroxypyruvic acid, idaric acid, isocitric acid, lactic acid, lyxaric acid, malic acid, mandelic acid, mannaric acid, methyllactic acid, mucic acid, phenyllacetic acid, pyruvic acid, quinic acid, ribaric acid, ribonic acid, saccharic acid, talaric acid, tartaric acid, tartronic acid, threaric acid, tropic acid, uronic acids, xylaric acid and analogs, derivatives, esters and salts thereof in amounts ranging from about 5 to about 50% by weight of the formulation.

Other keratolytic agents useful in the treatments of the invention include, but are not limited to, beta hydroxy acids such as salicylic acid and the like. In certain embodiments, the amount of salicylic acid is about 5% to about 30% by weight of the composition. In certain preferred embodiments, the amount of salicylic acid is from about 5% to about 20% by weight.

Other useful keratolytics may include, but are not limited to short chain carboxylic acids, having up to 6 carbon atoms in its skeleton; dicarboxylic acids, selected from the group consisting of malonic acid (propanedioic acid), succinic acid (butanedioic acid), glutaric acid (pentanedioic acid), adipic acid, pimelic acid, suberic acid, azelaic acid, sebacic acid, 1,11-undecanedioic acid, 1,12-dodecanedioic acid, 1,13-tridecanedioic acid, 1,14-tetradecanedioic acid and analogs, derivatives, esters and salts thereof; phenols; retinoids, selected from the group consisting of retinol, retinal, retinoic acid, retinyl acetate, retinyl palmitate, retinyl ascorbate, isotretinoin, tazarotene, adapalene, 13-c/s-retinoic acid, acitretin all-trans beta carotene, alpha carotene, lycopene, 9-cis-beta-carotene, lutein and zeaxanthin and analogs, derivatives, esters and salts thereof; papain, sulfur, glycolic acid, pyruvic acid, resorcinol, N-acetylcysteine, coal tar, and combinations of any of the foregoing. In general, the total amount of the keratolytic agent is from about 1% to about 60% by weight of the final composition.

A particularly preferred active agent with keratolytics activity is salicylic acid. Salicylic acid is a beta hydroxy acid. This colorless crystalline organic acid is widely used in organic synthesis and functions as a plant hormone. It is derived from the metabolism of salicin. In addition to being a compound that is chemically similar to but not identical to the active component of aspirin (acetylsalicylic acid), it is probably best known for its use in anti-acne treatments. The salts and esters of salicylic acid are known as salicylates.

The United States Food and Drug Administration recommends the use of sun protection when using skincare products containing salicylic acid (or any other BHA) on sun-exposed skin areas. Therefore, in certain embodiments of the present invention, sun exposure should be limited during therapy and sunscreen with a high SPF, e.g., SPF 20 or greater, should be used during and for 2 weeks after therapy has terminated. Therapy should also be discontinued if any redness, irritation or pain is experienced at or near the application site.

Protein denaturants are substances which are able to alter the 3-dimensional structure of protein (the tertiary structure of the polypeptide), mostly by forming additional secondary bonding such as hydrogen bonding and ion-dipole bonding on the component of the structure, i.e. the amino acid. Chaotropes such as urea or guanidine hydrochloride disrupt water interactions and help solubilize hydrophobic proteins and peptides. They also act as general protein denaturants, unfolding proteins and altering their three-dimensional structure. Ammoniumtetramethylenedithiocarbamate [ATMDC], ammoniumpyrrolidonedithocarbamate [APDC], tetramethylammoniumbromide [TMAB] and pentaalkylammoniumbromidehexaethyl [PAABHE] surfactants are stronger protein denaturants which may be useful in certain embodiments.

Organic compounds such as alcohols and carboxylic acids are able to denature proteins, and may be used in the treatments of the invention.

A preferred active agent is urea. Urea or carbamide is an organic compound with the chemical formula $(NH_2)_2CO$. The molecule has two amine (—$NH_2$) residues joined by a carbonyl (—CO—) functional group. Urea is a humectant produced naturally within the stratum corneum as part of the NMF and plays a critical role in moisture retention in the skin. Exogenous urea applied to the skin has high osmotic activity. Topically applied urea penetrates the skin by breaking hydrogen bonds in the outer layers of the stratum corneum to expose water-binding sites, below (a phenomenon known as hydrotopic solubilization). For this reason, urea may be used very effectively in topical moisturizing compositions. As a humectant, at concentrations lower than about 10%, a composition containing urea is intended as an everyday or occasional moisturizer. At concentrations significantly higher than about 10% (even up to 40%), topical compositions containing urea are effective treatments for severe cases of dry, rough skin, such as ichthyosis and psoriasis. Hydroxyethyl Urea is highly hygroscopic and offers excellent moisturizing benefit, and may also be beneficially included in the inventive treatments. Hydroxyethyl Urea delivers moisturization efficacy comparable to glycerin, while offering improved sensory perception in skin care products. Attributes include high speed of absorption, low gloss, low stickiness, and a low amount of residue on the skin.

In certain embodiments, the topical composition includes one or more hydrating agents (humectants) in effective amounts. Examples of suitable hydrating agents (humectants) include glycerine, propylene glycol, polyethylene glycol, polypropylene glycol, glyceryl triacetate, polyols such as sorbitol, xylitol and maltitol, polymeric polyols like polydextrose, or natural extracts like quillaia, lactic acid or urea; and mixtures thereof.

In certain embodiments, the invention involves the use of a known skin softener composition, comprising a combination of urea and salicylic acid in a white petroleum base, for topical application in the prevention and/or treatment of capsular contracture and scar tissue in the surgical implant patient. A method of preparation for this composition has been described in U.S. Pat. No. 7,097,847 (Reynolds), which states "[u]rea, salicylic acid and white petrolatum are all known as ingredients in commercially available topical products. Urea is used in topical compositions as an emollient, humectant as well as a keratolytic. Because urea is naturally present in the stratum corneum, it is considered a natural moisturizing factor. Salicylic acid possesses keratolytic activity. White petrolatum is a hydrocarbon base that is used in ointments, and it has the additional value of being an emollient and an occlusive."

In certain embodiments, the compositions comprise the enzyme papain and, optionally, urea. Papain is a protein-cleaving enzyme derived from papaya and certain other plants. The concentration of papain is from about 0.5% to about 40%, preferably from about 1% to about 20%, more preferably from about 1% to about 10% by weight of the final composition.

In certain embodiments the active agent comprises ammonium lactate present in an amount from about from about 5% to about 30%, more preferably about 5% to about 20% and most preferably from about 5% to about 15%. In certain other embodiments, the compositions comprise ammonium lactate and from about 5% to about 20% urea. In certain preferred embodiments, the compositions comprise ammonium lactate and about 12% to about 15% urea.

The compositions used in the methods of the present invention include a suitable carrier component for the active agent that provides compositions that are physically stable, e.g., the physical state of the composition upon packaging remains substantially constant over the shelf life of the product at room temperature. The compositions are also chemically stable which means, the components of the compositions do not chemically degrade to an unacceptable extent during the shelf life of the product at room temperature.

The compositions can be in solid or wax forms, semi solid ointments, creams, pastes, foams and gels and liquids such as lotions, suspensions, emulsions and solutions. In certain embodiments where greater penetration of the active agents through the stratum corneum is required, compositions that are more occlusive are preferred.

In certain embodiments wherein the composition e.g., wherein the composition is an ointment, the carrier comprises an occlusive oleaginous component such as white petrolatum.

Other components that may be present in the compositions of the invention, of any physical state, include but are not limited to agents identified in the following paragraphs.

Penetration enhancers which may include, but are not limited to a polyol, glycerol, ethylene glycol, propylene glycol, hexylene glycol, diethylene glycol, propylene glycol n-alkanols, a terpene, a di-terpene, a tri-terpene, a terpen-ol, limonene, 1-menthol, dioxolane, a sulfoxide, dimethylsulfoxide, dimethylformamide, methyl dodecyl sulfoxide, dimethylacetamide, dimethylisosorbide, a monooleate of ethoxylated glyceride, ozone, 2-(n-nonyl)-1,3-dioxolane, isopropyl myristate, isopropyl palmitate, ethyl acetate, butyl acetate, methyl proprionate, capric/caprylic triglycerides, octylmyristate, dodecylmyristate; myristyl alcohol, lauryl alcohol, lauric acid, lauryl lactate ketones; acetamide oleate, triolein, an alkanoic acid, caprylic acid dialkylamino acetate and a polyethylene glycol may be present in amounts from about 0.5% to about 20%.

Polyethylene glycol (PEG), is commercially available in a range of increasing molecular weights and viscosity. PEG having a molecular weight of 1000 or greater is a solid at room temperature, but softens near body temperature. Lower molecular weight PEGS are semi-solids while the lowest PEG products are liquids at room temperature.

Emollients which may include, but are not limited to mineral oil, petrolatum, polydecene, isohexadecane, fatty acids and alcohols having from 10 to 30 carbon atoms; pelargonic, lauric, myristic, palmitic, steraric, isostearic, hydroxystearic, oleic, linoleic, ricinoleic, arachidic, behenic, and euricic acids and alcohols; triglyceride esters, castor oil, cocoa butter, safflower oil, sunflower oil, jojoba oil, cottonseed oil, corn oil, olive oil, cod liver oil, almond oil, avocado oil, palm oil, sesame oil, squalene, Kikui oil, soybean oil, acetoglyceride esters, ethoxylated glycerides, ethoxylated glyceryl monostearate, alkyl esters of fatty acids having 10 to 20 carbon atoms, hexyl laurate, isohexyl laurate, isohexyl palmitate, isopropyl palmitate, decyl oleate, isodecyl oleate, hexadecyl stearate, decyl stearate, diisopropyl adipate, diisohexyl adipate, diisopropyl sebacate, laurly lactate, myristyl lactate, acetyl lactate; alkenyl esters of fatty acids having 10 to 20 carbon atoms, oleyl myristate, oleyl stearate, oleyl oleate, fatty acid esters of ethoxylated fatty alcohols, polyhydric alcohol esters, ethylene glycol mono and di-fatty acid esters, diethylene glycol mono- and di-fatty acid esters, polyethylene glycol, wax esters, beeswax, spermaceti, myristyl myristate, stearyl stearate, silicone oils, dimethicones, cyclomethicones, and mixtures thereof may be present in amounts from about 10% to about 90%.

Gelling agents which may include, but are not limited to polyacrylic acid polymers, carbomers, cellulose derivatives, poloxamers, poloxamines, chitosans, dextrans, pectins, natural gums, cellulose derivatives, ethyl cellulose, hydroxypropyl cellulose, hydroxyethyl cellulose, hydroxypropyl methyl cellulose (HPMC), carboxymethyl cellulose (CMC), and mixtures thereof may be present in amounts from about 1% to about 25%.

Humectants which may include, but are not limited to glycerin, propylene glycol, glyceryl triacetate, polyols, sorbitol, maltitol, polymeric polyols, polydextrose, quillaia, lactic acid, and mixtures thereof may be present in amounts from about 5% to about 50%.

Glycerin, widely considered to be an industry benchmark for skin moisturization due to its high moisturizing efficacy, has been known in the cosmetic industry for over 75 years. Glycerin is a colorless, odorless, and easy-to-use water-soluble liquid. It is normally added in the water phase and it can be post-added to an oil-in-water emulsion without special processing. It has broad compatibility over a wide pH range and with a variety of raw materials.

Alcohols which may include, but are not limited to ethanol and isopropyl alcohol, polyethylene glycols may be present in amounts from about 5 to about 80%.

Antioxidants which may include, but are not limited to all forms of Vitamin A including retinol and 3,4didehydroretinol, all forms of carotene including a-carotene, fl-carotene, gammacarotene, and delta-carotene, all forms of Vitamin C including D-ascorbic acid and Lascorbic acid, all forms of Vitamin E including a-tocopherol, fl-tocopherol, gammatocopherol, delta-tocopherol, tocoquinone, tocotrienol, Vitamin E esters which readily undergo hydrolysis to Vitamin E including Vitamin E acetate and Vitamin E succinate, and pharmaceutically acceptable Vitamin E salts such as Vitamin E phosphate, prodrugs of Vitamin A, carotene, Vitamin C, and Vitamin E, pharmaceutically acceptable salts of Vitamin A, carotene, Vitamin C, and Vitamin E, and mixtures thereof may be present in amounts from about 1% to about 90%.

In certain embodiments the present invention relates to methods for the treatment and prevention of the above-mentioned conditions comprising application of compositions of stable, uniform, water-washable ointment of a non-aqueous emulsion. The composition is comprised of (i) about 49.35% (w/w) of white petrolatum, (ii) about 0.9% (w/w) of polysorbate 80, (iii) about 6.1% (w/w) of PEG 40 sorbitan peroleate, (iv) about 3.65% (w/w) of polyoxyl 40 stearate, (v) about 11.0% (w/w) of glycerol, (vi) about 14.0% (w/w) of PEG-8, (vii) about 10.0% (w/w) of urea, and (viii) about 5.0% (w/w) of salicylic acid.

Stable pharmaceutical suspensions are physically and chemically stable during the shelf life of the composition. Shelf life may range from 6 months to 5 years. In certain embodiments, the composition is physically stable, i.e., does not separate during storage. Salicylic acid crystals do not migrate out of the ointment, creating an unstable preparation. In addition to the good sedimentation properties, the suspension remains uniform during storage; that is the component ingredients do not fall out of the suspension over time.

In certain embodiments, the water-free lipid base of the composition has the addition of hydrophillic emulsifiers that lead to a better disposition of the urea and salicylic acid. The emulsifiers add to the washable property of the composition in that the composition may be washed off the skin without the use of soaps or synthetic detergents.

In certain embodiments, the topical composition may be a semi-solid at room temperature but is easily absorbed into the stratum corneum. Such a composition can include petroleum-based liquids and solid fractions as skin protectants. The solid skin protectant can be present at concentration of up to about 50% of the compositions; protectants may include petrolatum or semi-synthetic hydrocarbons of the same nature as petrolatum. Mixtures of such ingredients may also be used. Liquid skin protectants can be petrolatum in the composition up to about 50% (w/w) of the composition and include a synthetic or semi-synthetic oleaginous liquid fraction. The liquid skin protectant can be mineral oil, which is a liquid mixture of hydrocarbon obtained from petroleum.

In certain embodiments, the compositions may include additional humectants which may include, but are not limited to glycerin, glycerol, butylene glycol, propylene glycol, sorbitol, triacetin, and combinations thereof can be used as the humectant and base component necessary for the discontinuous phase of the composition where a suspension is provided. Bases that are humectants have the additional benefit of hydrating the stratum corneum. In certain embodiments, the humectant can be present in the composition up to about 15% (w/w). In certain embodiments, glycerol is present in the composition at about 11% (w/w).

The humectant may be mixed with a non-aqueous thickener which may include, but are not limited to polyethylene glycol, hydroxyethyl cellulose, hydroxypropyl cellulose, carboxyvinyl polymers, acacia, tragacanth, synthetic and non-synthetic gums and mixtures thereof. In one embodiment, PEG-8 is used in the method to prepare the skin softening ointment.

In certain embodiments, various emulsifiers may be used in the process to prepare the composition of this invention. To increase the water solubility of some emulsifiers, polyoxyethylene groups are added through an ether linkage with one of their alcohol groups. The most widely used compounds are the polyoxyethylene sorbitan fatty acid esters. Closely related compounds include polyoxyethylene glyceryl and polyoxypropylene esters. It is also possible to have a direct ether linkage with the hydrophobic group as with a polyoxyethylene-stearyl ether or a polyoxyethylene-alkyl phenol. Other useful emulsifiers include acacia, tragacanth, oleic acid, stearic acid, cetyl stearyl alcohol, cetyl alcohol, lanolin, mineral oil, anionic emulsifying wax, polyethoxylated castor oil, hydroxypropyl cellulose, diethanolamine, polyxyethylene ether, monostearate glyceryl, lecithin, medium chain triglycerides, methyl cellulose, monoethanolamine, nonionic emulsifying wax, oleic acid, poloxamer, polyethyoxylated castor oil, polyoxyethylene ethers, polyoxyethylene fatty acid esters, polyoxyethylene stearates, propylene glycol alginate, sodium citrate, sodium lauryl sulfate, sodium phosphate monobasic, sorbitan fatty acid esters, stearic acid, triethanolamine, medium chain triglycerides and mixtures thereof.

The composition can be in the form of an emulsion. An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Emulsions can also be prepared from two non-miscible organic components such as an oil in oil emulsion. Either or both of the continuous phase and the discontinous phase may contain one or more excipients such as surfactants, emulsifiers, emulsion stabilizers, anti-oxidants, emollients, humectants, chelating agents, suspending agents, thickening agents, occlusive agents, preservatives, stabilizing agents, pH modifying agents, solubilizing agents, penetration enhancers, and other excipients.

Suitable emulsifiers include, but are not limited to, straight chain or branched fatty acids, polyoxyethylene sorbitan fatty acid esters sorbitan fatty acid esters, propylene glycol stearate, glyceryl stearate, polyethylene glycol, fatty alcohols, polymeric ethylene oxide-propylene oxide block copolymers, and combinations thereof.

Suitable surfactants include, but are not limited to, anionic surfactants, non-ionic surfactants, cationic surfactants, and amphoteric surfactants. Examples of anionic surfactants include, but are not limited to, ammonium lauryl sulfate, sodium lauryl sulfate, ammonium laureth sulfate, sodium laureth sulfate, alkyl glyceryl ether sulfonate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanol amine lauryl sulfate, triethanol amine lauryl sulfate, monoethanolamine cocoyl sulfate, monoethanolamine lauryl sulfate, sodium tridecyl benzene sulfonate, sodium dodecyl benzene sulfonate, sodium and ammonium salts of coconut alkyl triethylene glycol ether sulfate; tallow alkyl triethylene glycol ether sulfate, tallow alkyl hexaoxyethylene sulfate, disodium N-octadecylsulfosuccinnate, disodium lauryl sulfosuccinate, diammonium lauryl sulfosuccinate, tetrasodium N-(1,2-dicarboxyethyl)-N-octadecylsulfosuccinnate, diamyl ester of sodium sulfosuccinic acid, dihexyl ester of sodium sulfosuccinic acid, dioctyl esters of sodium sulfosuccinic acid, docusate sodium, and combinations thereof.

Examples of nonionic surfactants include, but are not limited to, polyoxyethylene fatty acid esters, sorbitan esters, cetyl octanoate, cocamide DEA, cocamide MEA, cocamido propyl dimethyl amine oxide, coconut fatty acid diethanol amide, coconut fatty acid monoethanol amide, diglyceryl diisostearate, diglyceryl monoisostearate, diglyceryl monolaurate, diglyceryl monooleate, ethylene glycol distearate, ethylene glycol monostearate, ethoxylated castor oil, glyceryl monoisostearate, glyceryl monolaurate, glyceryl monomyristate, glyceryl monooleate, glyceryl monostearate, glyceryl tricaprylate/caprate, glyceryl triisostearate, glyceryl trioleate, glycol distearate, glycol monostearate, isooctyl stearate, lauramide DEA, lauric acid diethanol amide, lauric acid monoethanol amide, lauric/myristic acid diethanol amide, lauryl dimethyl amine oxide, lauryl/myristyl amide DEA, lauryl/myristyl dimethyl amine oxide, methyl gluceth, methyl glucose sesquistearate, oleamide DEA, PEG-dislearate, polyoxyethylene butyl ether, polyoxyethylene cetyl ether, polyoxyethylene lauryl amine, polyoxyethylene lauryl ester, polyoxyethylene lauryl ether, polyoxyethylene nonylphenyl ether, polyoxyethylene octyl ether, polyoxyethylene octylphenyl ether, polyoxyethylene oleyl amine, polyoxyethyelen oleyl cetyl ether, polyoxyethylene oleyl ester, polyoxyethylene oleyl ether, polyoxyethylene stearyl amine, polyoxyethylene stearyl ester, polyoxyethylene stearyl ether, polyoxyethylene tallow amine, polyoxyethylene tridecyl ether, propylene glycol monostearate, sorbitan monolaurate, sorbitan monooleate, sorbitan monopalmitate, sorbitan monostearate, sorbitan sesquioleate, sorbitan trioleate, stearamide DEA, stearic acid diethanol amide, stearic acid monoethanol amide, laureth-4, and combinations thereof.

Examples of amphoteric surfactants include, but are not limited to, sodium N-dodecyl-β-alanine, sodium N-lauryl-β-iminodipropionate, myristoamphoacetate, lauryl betaine, lauryl sulfobetaine, sodium 3-dodecyl-aminopropionate, sodium 3-dodecylaminopropane sulfonate, sodium lauroamphoacetate, cocodimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2heptafluoropropane-hydroxyethyl)carboxymethyl betaine, stearyl bis-(2-hydroxypropyl)carboxymethyl betaine, oleyl dimethyl gamma-carboxypropyl betaine, lauryl bis-(2-hydroxypropyl)alpha-carboxyethyl betaine, oleamidopropyl betaine, coco dimethyl sulfopropyl betaine, stearyl dimethyl sulfopropyl betaine, lauryl dimethyl sulfoethyl betaine, lauryl bis-(2-hydroxyethyl)sulfopropyl betaine, and combinations thereof.

Examples of cationic surfactants include, but are not limited to, behenyl trimethyl ammonium chloride, bis(acyloxyethyl)hydroxyethyl methyl ammonium methosulfate, cetrimonium bromide, cetrimonium chloride, cetyl trimethyl ammonium chloride, cocamido propylamine oxide, distearyl dimethyl ammonium chloride, ditallowedimonium chloride, guar hydroxypropyltrimonium chloride, lauralkonium chloride, lauryl dimethylamine oxide, lauryl dimethylbenzyl ammonium chloride, lauryl polyoxyethylene dimethylamine oxide, lauryl trimethyl ammonium chloride, lautrimonium Y chloride, methyl-1-oleyl amide ethyl-2-oleyl imidazolinium methyl sulfate, picolin benzyl ammonium chloride, polyquaternium, stearalkonium chloride, sterayl dimethylbenzyl ammonium chloride, stearyl trimethyl ammonium chloride, trimethylglycine, and combinations thereof.

Suitable suspending agents include, but are not limited to, alginic acid, bentonite, carbomer, carboxymethylcellulose and salts thereof, colloidal oatmeal, hydroxyethylcellulose, hydroxypropylcellulose, microcrystalline cellulose, colloidal silicon dioxide, dextrin, gelatin, guar gum, xanthan gum, kaolin, magnesium aluminum silicate, maltitol, triglycerides, methylcellulose, polyoxyethylene fatty acid esters, polyvinylpyrrolidone, propylene glycol alginate, sodium alginate, sorbitan fatty acid esters, tragacanth, and combinations thereof.

Suitable antioxidants include, but are not limited to, butylated hydroxytoluene, alpha tocopherol, ascorbic acid, fumaric acid, malic acid, butylated hydroxyanisole, propyl gallate, sodium ascorbate, sodium metabisulfite, ascorbyl palmitate, ascorbyl acetate, ascorbyl phosphate, Vitamin A, folic acid, flavons or flavonoids, histidine, glycine, tyrosine, tryptophan, carotenoids, carotenes, alpha-Carotene, beta-Carotene, uric acid, pharmaceutically acceptable salts thereof, derivatives thereof, and combinations thereof.

Suitable chelating agents include, but are not limited to, EDTA, disodium edetate, trans-1,2-diaminocyclohexane-N,N,N'N'-tetraaceticacid monohydrate, N,N-bis(2-hydroxyethyl)glycine, 1,3-diamino-2-hydroxypropane-N,N,N',N'-tetraacetic acid, 1,3-diaminopropane-N,N,N',N'-tetraacetic acid, ethylenediamine-N,N'-diacetic acid, ethylenediamine-N,N'-dipropionic acid, ethylenediamine-N,N'-bis(methylenephosphonic acid), N-(2-hydroxyethyl)ethylenediamine-N,N',N'-triacetic acid, ethylenediamine-N,N,N',N'-tetrakis (methylenephosphonic acid), O,O'-bis(2-aminoethyl) ethyleneglycol-N,N,N',N'-tetraacetic acid, N,N-bis(2-hydroxybenzyl)ethylenediamine-N,N-diacetic acid, 1,6-hexamethylenediamine-N,N,N',N'-tetraacetic acid, N-(2-hydroxyethyl)iminodiacetic acid, iminodiacetic acid, 1,2- diaminopropane-N,N,N',N'-tetraacetic acid, nitrilotriacetic acid, nitrilotripropionic acid, nitrilotris(methylenephosphoric acid), 7,19,30-trioxa-1,4,10,13,16,22,27,33-octaazabicyclop[11,11,11]pentatriacontane hexahydrobromide, triethylenetetramine-N,N,N',N',N''',N'''-hexaacetic acid, and combinations thereof.

Suitable emollients include, but are not limited to, myristyl lactate, isopropyl palmitate, light liquid paraffin, cetearyl alcohol, lanolin, lanolin derivatives, mineral oil, petrolatum, cetyl esters wax, cholesterol, glycerol, glycerol monostearate, isopropyl myristate, lecithin, and combinations thereof thereof.

The compositions described herein may further contain sufficient amounts of at least one pH modifier to ensure that the composition has a final pH of about 3 to about 11. Suitable pH modifying agents include, but are not limited to, sodium hydroxide, citric acid, hydrochloric acid, acetic acid, phosphoric acid, succinic acid, sodium hydroxide, potassium hydroxide, ammonium hydroxide, magnesium oxide, calcium carbonate, magnesium carbonate, magnesium aluminum silicates, malic acid, potassium citrate, sodium citrate, sodium phosphate, lactic acid, gluconic acid, tartaric acid, 1,2,3,4-butane tetracarboxylic acid, fumaric acid, diethanolamine, monoethanolamine, sodium carbonate, sodium bicarbonate, triethanolamine, and combinations thereof.

Preservatives can be used to prevent the growth of bacteria, fungi and other microorganisms. Suitable preservatives include, but are not limited to, benzoic acid, butylparaben, ethyl paraben, methyl paraben, propylparaben, sodium benzoate, sodium propioniate, benzalkonium chloride, benzethonium chloride, benzyl alcohol, cetypyridinium chloride, chlorobutanol, phenol, phenylethyl alcohol, thimerosal, and combinations thereof.

The compositions can also contain known adjuvants and additives, such as bactericides, fungicides, virucides, light filter substances, active ingredients with a cooling action, antioxidants, plant extracts, screening agents, odor absorbers, skin-coloring agents screening agents, odor absorbers, skin-coloring agents, perfumes, antifoams, dyes, pigments which have a coloring action, thickeners, surface-active substances, emulsifiers, emollients, moisturizers and/or humectants, fats, oils, waxes, alcohols, polyols, polymers, foam stabilizers, electrolytes, organic solvents, silicone derivatives or chelating agents.

Skin soothing agents may include, but are not limited to, aloe, avocado oil, green tea extract, hops extract, chamomile extract, colloidal oatmeal, calamine, cucumber extract, and combinations thereof.

In certain embodiments, the compositions used in the methods of the present invention also include sunscreens. Sunscreens may include, but are not limited to, p-Aminobenzoic acid, Avobenzone, Cinoxate, Dioxybenzone, Homosalate, Menthyl anthranilate, Octocrylene, Octyl methoxycinnamate, Octyl salicylate, Oxybenzone, Padimate O, Phenylbenzimidazole sulfonic acid, Sulisobenzone, Titanium dioxide, Trolaminie salicylate, Zinc oxide, 4-methylbenzylidene camphor, Methylene Bis-Benzotriazolyl Tetramethylbutylphenol, Bis-Ethylhexyloxyphenol Methoxyphenyl Triazine, Terephthalylidene Dicamphor Sulfonic Acid, Drometrizole Trisiloxane, Disodium Phenyl Dibenzimidazole Tetrasulfonate, Diethylamino Hydroxybenzoyl Hexyl Benzoate, Octyl Triazone, Diethylhexyl Butamido Triazone, Polysilicone-15, and combinations thereof.

In certain embodiments, the carrier component may comprise from about 25% to about 95% of the formulation and may comprise any combination of the foregoing carrier ingredients.

As will be appreciated by one of ordinary skill in the art, conventional pharmaceutical manufacturing processes are suitable for manufacture of the compositions for use in the methods of treatment and prevention of present invention. The general process involves combining the carrier components with the active agents to obtain a uniform mixture utilizing current Good Manufacturing Practices ("cGMP"), e.g., as set forth by the United States Food and Drug Administration in U.S. 21 C.F.R. Parts 210 and 211.

Where the compositions are thick ointments, it may be preferable to heat the carrier component, e.g., white petrolatum to facilitate mixing. Where the active agent or other component exists in dry powder form, in certain embodiments, it may be preferable to levigate the active agents with the use of a suitable liquid such as glycerin prior to mixing with the carrier component.

In certain embodiments, the compositions are prepared by an anhydrous method; that is, it has no water in the process. In certain embodiments, prior to manufacture, the mixing vessel is placed under a vacuum of up to −1000 mbar to displace all water out of the system. In certain embodiments, the composition is a water-washable semisolid, nonaqueous emulsion ointment. In certain embodiments, the resulting salicylic acid/urea product is highly occlusive and highly water-washable. In certain embodiments, the composition is an anhydrous emulsion comprised of a non-aqueous base, at least one emulsifier and a humectant and a non-aqueous thickener.

In one embodiment, the composition may be prepared according to the procedure described in U.S. Pat. No. 7,097,847 ((Reynolds) by (a) heating and mixing a humectant and a non-aqueous thickener under vacuum in a first vessel; (b) introducing urea under vacuum into the mixture of step (a); (c) heating and mixing the contents of step (b) under vacuum, at a temperature sufficient to dissolve the urea; (d) heating and mixing a non-aqueous base and at least one emulsifier in a second vessel, whereby the non-aqueous base liquefies; (e) drawing by vacuum the mixture from step (d) into the mixture in the first vessel; (f) mixing, heating and homogenizing and the contents of step (e) under vacuum; (g) cooling, mixing and homogenizing the mixture of step (f) to a congealing temperature under vacuum; (h) cooling the mixture of step (g); (i) drawing by vacuum salicylic acid into the mixture of step (h); (j) recirculating the mixture of step (i) under vacuum; and, (k) cooling the mixture of step (j) under vacuum. The composition according to this embodiment may provide, e.g., a composition having the following formula: (a) about 49.35% white petrolatum; (b) about 0.9% polysorbate 80; (c) about 6.1% PEG-40 Sorbitan Peroleate; (d) about 3.65% polyoxyl 40 stearate; (e) about 11% glycerol; (f) about 14% PEG-8; (g) about 10% urea and, (h) about 5% salicylic acid.

In certain embodiments, the manufacturing method optimizes the use of temperature and vacuum to minimize moisture which results in the degradation urea, and the resultant unwanted byproducts of ammonia and carbon dioxide, and the concomitant formation of an unpleasant smell.

In certain preferred embodiments, the invention involves using formulations preferably comprising about 5% salicylic acid and about 10% urea, which formulations were previously used as a skin softener. Specific examples of suitable compositions for use in the present invention include products commercially available from Kerasal®, including but not limited to (i) Kerasal® Original Foot Ointment: One Step Exfoliating Moisturizer Therapy, having as main ingredients: salicylic acid 5% and urea 10%; and having as other ingredients: white petrolatum, PEG-8, glycerin, urea, PEG-40 sorbitan peroleate, salicylic acid, PEG-40, stearate, polysorbate-80; (ii) Kerasal® Foot Care Lotion, having as its main ingredient ammonium lactate 10%; other ingredients are purified water, ammonium lactate, petrolatum, glycerin, propylene glycol, light mineral purified water, ammonium lactate, petrolatum, glycerin, propylene glycol, light mineral oil, glyceryl monostearate, methylcellulose, magnesium aluminum silicate, polyoxyl 40 stearate, laureth-4, polyoxyethylene 100 stearate, cetyl alcohol, methylparaben, propylparaben and for pH adjustment: ammonium hydroxide and lactic acid; (iii) Kerasal® Ultra20 Foot Care Lotion, having as its main ingredients urea 20% and ammonium lactate 5%; other ingredients being water, urea, mineral oil, ammonium lactate, petrolatum, propylene glycol, glyceryl stearate SE, glyceryl stearate, glycerin, cetyl alcohol, PEG-100 stearate, steareth-2, xanthan gum, disodium EDTA, phenoxyethanol, methylparaben, butylparaben, ethylparaben, propylparaben, isobutylparaben.

The methods of the present invention for treatment and/or prevention or substantial prevention of capsular contracture comprise topical application of the compositions of the present invention. In certain embodiments, it is preferable that the external surface of the affected area (e.g., the skin surrounding the implant), is washed and dried prior to application. In certain embodiments, the composition is applied one or more times daily, e.g., twice daily. In certain embodiments, a thin film of the compositions disclosed herein is applied to the external surface. In certain embodiments, the compositions are applied with vigorous message to the affected area.

In certain embodiments, enhanced absorption is obtained with application of the compositions of the invention following a hot shower or bath. In certain embodiments, an occlusive dressing (e.g., a hydrogel or a bandage), or tight clothing (e.g., sports bras), will also enhance the result.

In certain embodiments, continued daily use will yield optimal results.

In certain embodiments, compression or pressure is exerted when massaging to break up the existing capsule.

In certain embodiments, daily application, e.g., twice daily application should continue for a minimum of 2 to 4 weeks or until there is a return to a grade one capsule, or no further continued improvement in capsule softening occurs for a week. In certain embodiments, optimal results are best maintained with daily continued application.

Response to this treatment method may vary depending on the stage, composition and timing of capsular contracture as well as the length of twice daily application. Lack of patient compliance will adversely affect the ultimate result.

The composition should not be used on infected, irritated or broken skin, or directly on or over a tattoo.

Diabetics should use only under a doctor's supervision.

DETAILED DESCRIPTION OF PREFERRED EMBODIMENTS

The following examples are purely illustrative without any intention of being limiting. It is to be understood that the invention is not limited in its application to the details of construction and the arrangement of the components set forth in the following description. The invention includes other embodiments and can be practiced and implemented in various ways. It is also to be understood that the phraseology and terminology employed herein is for the purpose of description only and should not be regarded as limiting.

EXAMPLE 1

An ointment having 5% salicylic acid and 10% urea is prepared in a carrier containing white petrolatum, PEG-8, glycerin, PEG-40 sorbitan peroleate, PEG-40, stearate and polysorbate-80 in accordance with the procedures set forth in U.S. Pat. No. 7,097,847. The composition is prepared by combining the carrier components except for glycerin, in a suitable mixing vessel at 50° C. for about 5 minutes or until the mixture is uniform. One third of the glycerin is mixed with the salicylic acid to form a paste, the remaining glycerin is added along with the urea and mixed until uniform utilizing convention mixing equipment. The carrier mixture is then added to the glycerin and active agent mixture and mixed until uniform. The composition is allowed to cool and packaged in opaque polypropylene containers and aluminum tubes in quantities of 2, 4, 8 and 16 ounces.

EXAMPLE 2

Compositions with Salicylic Acid Plus Urea and Ammonium Lactate

In Example 2, five preparations having the ingredients set forth in Table 1 below are prepared according the general manufacturing process used in Example 1.

TABLE 1

| Salicylic Acid (% w/w) | Urea (% w/w) | Ammonium Lactate (% w/w) | Lanolin (% w/w) | Petrolatum (% w/w) | Mineral Oil (% w/w) | Water (% w/w) |
|---|---|---|---|---|---|---|
| 5-30 | 5-20 | — | — | 50-90 | — | — |
| 5-30 | 5-20 | — | 50-90 | — | — | — |
| 5-30 | 5-20 | — | 15-25 | 25-75 | — | — |
| 5-30 | 5-20 | — | 15-25 | 15-50 | 10-25 | — |
| — | 5-20 | 5-20 | 20 | 50 | 10 | 20 |

EXAMPLE 3

Ammonium Lactate 5% Urea 20% Lotion

In Example 3, an ammonium lactate and urea lotion composition containing water, mineral oil, petrolatum, propylene glycol, glyceryl stearate SE, glyceryl stearate, glycerin, cetyl alcohol, PEG-100 stearate, steareth-2, xanthan gum, disodium EDTA, phenoxyethanol, methylparaben, butylparaben, ethylparaben, propylparaben, isobutylparaben is prepared according to conventional manufacturing procedures.

EXAMPLE 4

Ammonium Lactate 5% Urea 20% Gel

In Example 4, an ammonium lactate and urea gel composition having the components set out in Table 2 is prepared.

TABLE 2

| Ingredient | % (w/w)t |
| --- | --- |
| Ammonium Lactate | 5 |
| Urea | 20 |
| Ethanol % (v) | 40 |
| Propylene glycol % (v) | 5 |
| Deionized water | QS |
| Carbopol | 5 |
| NaOH | 5 |
| Isopropyl myristate | 10 |

Clinical Cases

Patient #1

This patient was a 49-year-old female with a history of Crest syndrome. The patient was diagnosed with a grade 2 infiltrating ductal carcinoma of her right breast. The patient had a bilateral mastectomy with immediate saline implants (125 cc) reconstruction. Three months after the reconstruction, she developed a capsular fold in her left superior breast and bilateral Grade 3 capsular contracture. This prompted a first revision, comprising bilateral capsulectomies and implant exchange. Treatment with Aleve and massage were without result. Three months thereafter, recurrence of the capsular fold and capsule on the left warranted another capsulectomy on the left side.

Three months later bilateral recurrence of the capsule prompted referral to a surgeon for reconstruction with cohesive silicone implants (410 Inamed). Despite the placement of 410 implants, the capsules recurred and the reconstructive surgeon proposed the complete and definitive removal of the implants. The patient tried Singulair without improvement.

The patient then began the application of the composition of the invention (5% salicylic acid, 10% urea in a white petroleum base as in Kerasal One Step Exfoliating Moisturizer formulated as an ointment on a twice-a-day regimen. Within two weeks the capsules softened to a Grade 1. The reconstructive surgeon agreed that no further surgery was necessary. The patient thereafter maintained daily use of the ointment for prevention of recurrence. Additional daily use by this patient of ammonium lactate 5% and urea 20% as kerasal Ultra 20 daily for a month and secondly a composition of salicylic acid 5% and 12% Salicylic acid 5% and Urea 12%, Aloe, Vitamin A and Vitamin E white petrolatum, PEG-8, glycerin, urea, PEG-40 sorbitan peroleate, salicylic acid, PEG-40 stearate, retinyl palmitate, tocopheryl acetate, aloe barbadensis leaf juice, polysorbate-80 as Kerasal Professional Exfoliating Moisturizing Foot Ointment used also for a month both yielded successful maintenance of the Grade one capsules.

Patient #2

This patient was a 77 year-old female with infiltrating Grade 3 ductal carcinoma of her right breast. Her past medical history was significant for coronary disease and atrial fibrillation. She underwent a single stage immediate reconstruction with 176 cc silicone implants, as well as a right side mastopexy. The patient was treated with neoadjuvant chemotherapy with Femara.

Her post-operative course was uncomplicated; however, six months later she developed a grade 3 capsule on the left reconstructed breast. She began a treatment regimen with Kerasal One Step Exfoliating Moisturizer the ointment of the invention, and her capsule reversed to a Grade 1 within three weeks. She thereafter continued to use the ointment daily.

Patient #3

This patient was a 48-year-old female with a history of Stage III lobular carcinoma. She underwent a bilateral breast reconstruction with tissue expanders in February 2006, and one month later she underwent a bilateral ovariectomy. Within two years the patient developed bilateral Grade 3 capsules which gradually progressed to Grade 4. Pain was interfering with her sleep on an intermittent basis. The patient's primary plastic surgeon discussed with the patient the option of implant removal.

Three years post-operatively, the patient began a twice-a-day treatment regimen with Kerasal One Step Exfoliating Moisturizer the ointment of the invention and noticed a softening of the capsules within 3 days. She continued its use for four weeks and became asymptomatic, her capsules improving to a Grade 1. She thereafter continued to maintain prophylactic daily use of the ointment.

Patient #4

This patient was a 52-year-old female who had an immediate reconstruction with a tissue expander following a right mastectomy. The mastectomy was followed by radiotherapy and resulted in encapsulation of the right breast. She had multiple surgeries for capsular contraction with removal of the capsule and implant exchange. She failed all three revisions and almost five years after the mastectomy presented with chest wall pain and a Baker Capsule 4. She was seen for evaluation of tram (transverse rectus abdominis) flap surgery.

Pre-operatively, the patient was treated with Kerasal One Step Exfoliating Moisturizer for two weeks and a marked improvement and softness of her irradiated skin was seen. The changes included a decrease in pigmentation and general improvement in skin texture and color. Overall, she improved to a Grade 3 capsule.

Patient #5

This patient was a 50-year-old female who underwent a bilateral mastectomy for a grade 1 infiltrating lobular carcinoma of her right breast. The patient had a significant family history of breast cancer. She underwent a two stage breast reconstruction with tissue expanders, and four months later, after completion of chemotherapy, the second stage was performed with the insertion of 700 cc silicone implants. Three months thereafter the patient developed a Grade 3 capsule on the right side and was treated with Kerasal One Step Exfoliating Moisturizer for two weeks. The capsule improved to a Grade 2. She was advised to continue using the ointment to be evaluated for further improvement.

Patient #6

This patient was a 33-year-old female who underwent a left mastectomy for infiltrating lobular carcinoma. She underwent a two stage saline reconstruction with silicone implant followed by XRT. She subsequently developed a capsule on the left breast. She later had a capsulotomy and exchange with silicone implant. She underwent a controlateral mastectomy with two stage reconstruction with silicone implants two years later. Ultimately the worsening of her capsule on the left prompted a bilateral reconstruction with tram flaps. She subsequently desired a small augmentation of her TRAM flaps with silicone implants. The recurrence of the capsule to a Grade 3 on the left prompted the start of the Kerasal One Step Exfoliating Moisturizer Kerasal One Step Exfoliating Moisturizer ointment therapy. She noticed a marked improvement after two weeks and softened to a Grade 2.

Patient #7

This patient was a 56-year-old who was diagnosed with left invasive intraductal carcinoma of her left breast (Stage II A)) in 1999. Her treatment at the time of diagnosis consisted of chemo, lumpectomy and irradiation. This lead to an indurated scar tissue area in the 12 O'clock position and irradiation skin changes. Placed on the Kerasal One Step Exfoliating Moisturizer ointment Jun. 24, 2009 and improved after 2 weeks from a Grade III to II.

Patient #8

This patient was a 54-year-old diagnosed with invasive ductal CA of her right breast. She had a Right mastectomy and axillary node dissection followed by TE reconstruction on (May 8, 2007). Post operatively she underwent chemotherapy and radiation. Feb. 19, 2008 she underwent a TE exchange for a silicone implant with Alloderm and a capsulectomy. On Feb. 17, 2009 she underwent a second capsulectomy and implant exchange. She developed an advanced Grade 3 capsule with irradiated skin. Placed on Kerasal One Step Exfoliating Moisturizer the ointment Jul. 28, 2009, returned after two weeks with marked improvement, Grade 2 capsule and reverse radiation changes.

EQUIVALENTS

The foregoing written specification is sufficient to enable one skilled in the art to practice the invention. Indeed, various modifications of the above-described means for carrying out the invention which are obvious to those skilled in the art are intended to be within the scope of the following claims.

What is claimed is:

1. A method of treating capsular contracture, comprising topically applying to a human on an affected area which has developed or is at risk of developing capsular contracture, a topical composition containing:
    an amount of a pharmaceutically acceptable and topically active ingredient effective to treat said capsular contracture, said active ingredient comprises:
    a keratolytic comprising salicylic acid, and
    a protein denaturant comprising urea.

2. The method of claim 1, further comprising washing with warm water and drying the affected area prior to applying the topical composition.

3. The method of claim 2, further comprising applying the composition at least once daily to the affected area and massaging the affected area.

4. The method of claim 3, further comprising applying heat to the affected area prior to applying the topical composition.

5. The method of claim 1, wherein the keratolytic further comprises an agent selected from the group consisting of an alpha hydroxy acid, a beta hydroxy acid and combinations thereof.

6. The method of claim 1, wherein the composition further comprises a conjugate base of lactic acid.

7. The method of claim 1, wherein the composition further comprises ammonium lactate.

8. The method of claim 4, wherein the composition further comprises ammonium lactate.

9. The method of claim 4, further comprising administering the topical composition in a form selected from the group consisting of a solution, lotion, gel, foam, cream, ointment and paste.

10. The method of claim 1, wherein the composition comprises salicylic acid in a concentration from about 5% to about 30% by weight and urea in a concentration of from about 5% to about 20%.

11. The method of claim 1, further comprising preparing the topical composition as a stable, uniform water-washable ointment of anon-aqueous emulsion.

12. The method of claim 1, wherein the composition further comprises ammonium lactate in a concentration from about 5% to about 30% by weight and urea in a concentration of from about 5% to about 20%.

13. The method of claim 10, wherein the composition comprises urea in a concentration from about 12 to about 15% (w/w).

14. The method of claim 1, wherein the composition is applied fur at least 2 weeks.

15. The method of claim 1, further comprising implanting into the patient prior to application of the topical composition an implant selected from the group consisting of a breast implant, a calf implant, a buttocks implant, a pacemaker, and a defibrillator.

16. A method of treating capsular contracture, comprising topically applying to a human on a post-surgical implant area which has developed or is at risk of developing capsular contracture a topical composition comprising a protein denaturant comprising from about 5 to about 20% (w/w) urea together with a keratolytic comprising salicylic acid.

17. The method of claim 16, further comprising the steps of:
    washing and drying the post-surgical implant area prior to applying the topical composition,
    applying heat to the post-surgical implant area prior to applying the topical composition
    applying the topical composition at least once daily to the affected area and massaging the affected area.

18. The method of claim 17, further comprising preparing the topical composition as a stable, uniform water-washable ointment of a non-aqueous emulsion.

19. A method of treating capsular contracture, comprising:
    preparing a topical composition comprising from about 5 to about 20% (w/w) urea together with salicylic acid as a stable, uniform water-washable ointment of a non-aqueous emulsion,
    topically applying the topical composition at least once daily to a human on a post-surgical implant area which has developed or is at risk of developing capsular contracture,
    massaging the post-surgical implant area, and
    applying heat to the post-surgical implant area prior to applying the topical composition.

* * * * *